United States Patent
Nadeau

(10) Patent No.: US 6,709,888 B2
(45) Date of Patent: Mar. 23, 2004

(54) METHOD OF DECAPSULATING A PACKAGED COPPER-TECHNOLOGY INTEGRATED CIRCUIT

(75) Inventor: Julie M. Nadeau, Austin, TX (US)

(73) Assignee: Motorola, Inc., Schaumburg, IL (US)

( * ) Notice: Subject to any disclaimer, the term of this patent is extended or adjusted under 35 U.S.C. 154(b) by 0 days.

(21) Appl. No.: 10/205,865

(22) Filed: Jul. 26, 2002

(65) Prior Publication Data

US 2004/0018651 A1 Jan. 29, 2004

(51) Int. Cl.[7] .................. H01L 21/44; H01L 21/302; B44C 1/22
(52) U.S. Cl. .................. 438/106; 438/745; 216/108
(58) Field of Search .................. 438/15, 106, 127, 438/745; 216/2, 13, 83, 96, 100, 108

(56) References Cited

U.S. PATENT DOCUMENTS

| | | | | |
|---|---|---|---|---|
| 4,826,556 A | * | 5/1989 | Kobayashi | 156/345 |
| 5,244,539 A | * | 9/1993 | McGrath et al. | 156/656 |
| 5,443,675 A | | 8/1995 | Wensink | |
| 5,766,496 A | * | 6/1998 | Martin | 216/56 |
| 5,783,098 A | * | 7/1998 | Martin et al. | 216/56 |
| 5,990,543 A | * | 11/1999 | Weaver et al. | 257/666 |
| 6,043,100 A | * | 3/2000 | Weaver et al. | 438/4 |
| 6,368,886 B1 | * | 4/2002 | Van Broekhoven et al. | 438/15 |
| 6,387,206 B1 | | 5/2002 | Ghaemmaghami et al. | |
| 6,395,129 B1 | | 5/2002 | Vu et al. | |
| 6,429,028 B1 | * | 8/2002 | Young et al. | 438/4 |

FOREIGN PATENT DOCUMENTS

| | | | | |
|---|---|---|---|---|
| JP | 60059742 A | * | 4/1985 | H01L/21/56 |
| JP | 63268250 A | * | 11/1988 | H01L/21/56 |

* cited by examiner

Primary Examiner—Evan Pert
Assistant Examiner—Scott B. Geyer
(74) Attorney, Agent, or Firm—James L. Clingan, Jr.; Robert L. King

(57) ABSTRACT

A method of removing a portion of a molding compound encapsulant from around an integrated circuit die having copper-technology (CT) does not damage or significantly remove the copper. Fuming nitric acid and fuming sulfuric acid are mixed at a ratio of between 3:1 to 6:1 and heated to a relatively low temperature such as sixty degrees Celsius or less. In one form, a ratio of 4:1 and a temperature of fifty degrees Celsius are time efficient for removing a molding compound used as the encapsulant. The heated mixed acids are applied to the encapsulated integrated circuit in an etch chamber and the encapsulant is removed without significant reduction of the copper.

16 Claims, 1 Drawing Sheet

METHOD OF DECAPSULATING A PACKAGED COPPER-TECHNOLOGY INTEGRATED CIRCUIT

FIELD OF THE INVENTION

This invention is related to decapsulating packaged integrated circuits and, more particularly, those packaged integrated circuits made using copper-technology and encapsulated by a mold compound.

RELATED ART

Integrated circuits are often encapsulated in a mold compound. After such encapsulation, it can be difficult to perform subsequent failure analysis of the integrated circuit because it has been encapsulated. One of the techniques, which is mechanical, used to expose the integrated circuits is to grind the encapsulant back until the integrated circuit has been exposed. The encapsulant can also be cut along the sides. A disadvantage of the mechanical approach is the difficulty in knowing when to stop the grinding. Another disadvantage is that any wires will be ground away.

Chemical processes that can remove the mold compound are generally preferred. The typical chemicals used for this are nitric acid and sulfuric acid. Nitric acid has been quite successfully used for integrated circuits using aluminum technology but not with those using the more recent copper-technology. The nitric acid not only removes the mold compound but also the upper copper layer. If this happens, the top interconnect layer is not available for failure analysis. An example of an important test is the wire pull and ball shear test. This is a test of the wire-to-pad bond that is at the upper layer. Sulfuric acid also causes the same problem.

Thus, there is a need for a technique for chemically removing encapsulant of a packaged copper-technology integrated circuit without damaging the copper.

BRIEF DESCRIPTION OF THE DRAWINGS

The present invention is illustrated by way of example and not limited by the accompanying figures, in which like references indicate similar elements, and in which.

Skilled artisans appreciate that elements in the figures are illustrated for simplicity and clarity and have not necessarily been drawn to scale. For example, the dimensions of some of the elements in the figures may be exaggerated relative to other elements to help improve the understanding of the embodiments of the present invention.

DETAILED DESCRIPTION OF THE DRAWINGS

Decapsulation of a copper technology integrated circuit encapsulated in a mold compound is achieved using a predetermined ratio of fuming nitric acid to fuming sulfuric acid at a predetermined temperature. The combination of the high concentration of nitric acid and high concentration of sulfuric acid is believed to be particularly effective because the way that these two acids remove copper are different and counteract each other. Thus, in the proper combination and at the proper heat the copper is only minimally removed during the removal of the mold compound. This is better understood with respect to the following description.

Figure 1:
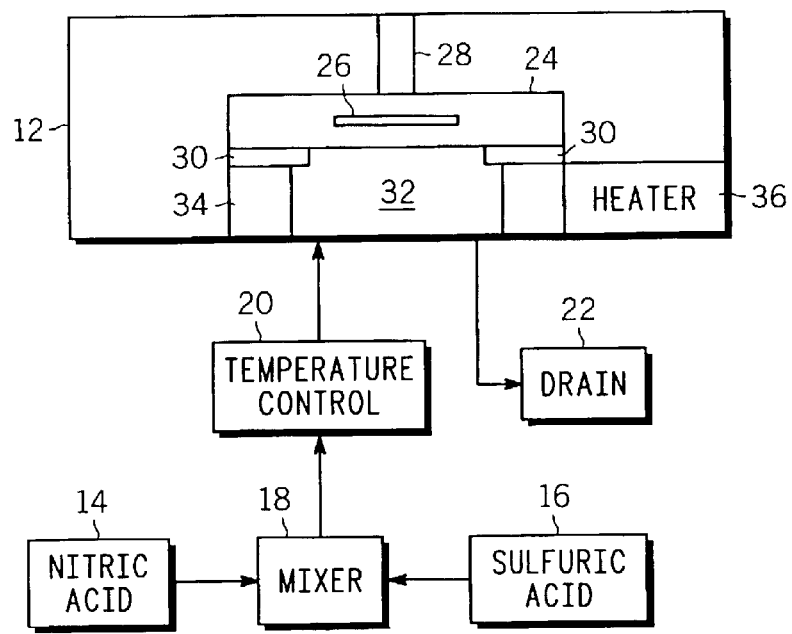
FIG. 1 is a diagram of a layout for performing decapsulation according to a preferred embodiment of the invention.

Shown in FIG. 1 is an etcher 10 comprising a housing 12, a nitric acid container 14, a sulfuric acid container 16, a mixer 18, a temperature control 20, a drain 22, a pressure plate 28, a gasket 30, a mixing region 32, a head 34, and a heater 36. Also shown in FIG. 1 is a packaged copper technology (CT) integrated circuit (IC) 24 having mold compound surrounding a CT IC 26. Mixer 18 is coupled to the nitric acid and sulfuric acid containers 14 and 16, respectively. Mixer 18 receives these acids at a predetermined rate and mixes them. Temperature control 20 is coupled to the mixer 18 and mixing region 32. The mixed acids are heated to a controlled temperature by temperature control 20 and provided to the mixing area 32. Drain 22 is coupled to mixing region 32 and removes the used mixed acids at a controlled rate. Packaged CT IC 24 has a portion exposed to mixing region 32 that is at least as large as the CT IC 26. This amount of exposure is selected by choosing the size of gasket 30. Gasket 30 provides a seal between head 34 and packaged CT IC 24. Head 34 which is between gasket 30 and housing 12 is coupled to heater 36. Heater 36 controls the temperature of head 34. Thus the mixed acids and head 34 can be at the same temperature to control the temperature of the mixed acids upon application to the exposed portion of packaged CT IC 24.

Figure 2:
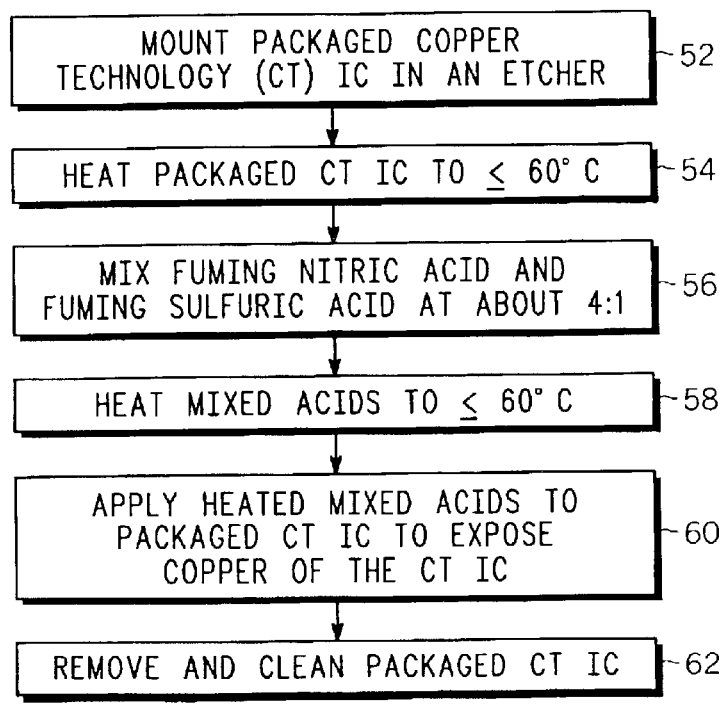
FIG. 2 is a flow chart of a method for performing decapsulating according the preferred embodiment of the invention.

The use of etcher is further understood by reference to the flow diagram of FIG. 2. Shown in FIG. 2 are steps 52, 54, 56, 58, 60, and 62. Step 52 is mounting the packaged CT IC in the etcher. This is achieved using gasket 30 to seal mixing region 32 with packaged CT IC 24 and expose the portion of the mold compound to be etched, which exposed portion is aligned with and larger than CT IC 26. Step 54 is heating Packaged CT IC 24 via heater 36, head 34, and gasket 30. The preferred temperature is in the range of 45 to 55 degrees Celsius. The temperature should particularly be below 60 degrees Celsius to achieve the desired effect of minimal copper removal. Lower temperatures than 45 degrees Celsius are considered slower in etch rate than desirable but effective in achieving the desired result. Thus, there should be heating but to a temperature below 60 degrees Celsius.

Step 56 is mixing the fuming nitric acid with the fuming sulfuric acid at a four to one ratio. The mixture may be effective at lower and higher ratios but not significantly so. A two to one ratio of nitric acid to sulfuric acid has been found to exhibit the problem of excessive copper removal. A three one to one ratio was also found to provide excessive removal of the copper. Thus the ration should be at least greater than three to one with four to one being optimum. Using just fuming nitric acid has been found to be a problem also so high ratios of nitric acid to sulfuric acid should also be avoided. A ratio of less than seven to one should be used. Thus a range of between greater than three and less than six to one should be the ratio of nitric acid to sulfuric acid with the preferred ratio at 3.5 to 4.5 to one.

Step 58 is heating the mixed acids to less than or equal to sixty degrees Celsius. This temperature is preferably the same as the temperature of the gasket 30, head 34, and packaged CT IC 24. It is not essential, however, for at least some benefit that these two temperatures be the same. Typical etchers that are currently available have just one heat control so the temperatures being the same is not only considered the most desirable but also likely to the only choice available. The criteria for the desired temperature is the same as for he step 54. The temperature should be elevated but not above sixty degrees Celsius. If the temperature is not elevated, the etch rate of the mold compound is too slow. If the temperature is elevated above sixty degrees, the removal of copper becomes excessive. The optimum temperature is believed to be fifty degrees Celsius. The desired range is plus or minus five degrees so that the desired temperature range is forty-five to fifty-five degrees.

Step 60 is applying the mixed acids to the exposed portion of the packaged CT IC 24 to expose but not remove the copper. The mold compound is removed using these mixed acids at these desired temperature ranges and ratios. The removal of copper has been found to be less than five percent. The copper bond pads remain and a "wire pull and ball shear" test can be performed. Further, even if copper wiring is used for wirebonding, these wires will remain and may be inspected. The effect of the use of this mixture at these temperatures and ratios is that minimal damage is done to the copper layer, which is on top of the CT IC 24, while effective removing the mold compound aligned to the CT IC 24. It is preferable that this step 60 not be started until step 54 has achieved temperature stability of gasket 30, head 34, and packaged CT IC 24. All the surfaces of mixing region 32 should be at the desired end temperature prior to the mixed acids reaching mixing region 32.

Step 62 is the final step and is the routine step of removing and cleaning the packaged CT IC 24. After step 62, decapsulation is complete and tests may be performed on all aspects of the CT IC 24 including the upper copper layer.

The use of fuming nitric acid and fuming sulfuric acid is considered significant. These fuming acids are liquid and are apparently named "fuming" because upon exposure to air they generate noticeable fumes. To be considered fuming, an acid must be of very high concentration. Exemplary fuming acids are red fuming nitric acid and yellow fuming nitric acid. Yellow fuming nitric acid is typically 90–98 percent. Red fuming nitric acid is even higher at typically 115 percent. Yellow fuming at 98 percent is preferred because it is less expensive and less volatile than red fuming but more concentrated than 90 percent. That it is less volatile makes it easier to work with. If red fuming nitric acid is used, it may be desirable to adjust the ratio downward but still not below three to one. If yellow fuming at 90 percent is used, then it may be desirable to adjust the ratio slightly upward but still not above six to one. Fuming sulfuric acid is available in at least twenty percent and thirty percent. The use of twenty percent is preferable because it is cheaper, but thirty percent could be used. If so, reducing the ratio of nitric acid to sulfuric should be also be increased to offset the increase in the percentage of the sulfuric acid but should still not need to exceed six to one.

Mold compounds used for encapsulation of integrated circuits have much in common but are not identically the same. The primary difference in effect is the etch rate of the mold compound. The process shown in FIG. 2 has been effective in achieving the desired result of removing the mold compound with only minimal removal of the copper. The fastest time has been about one and half minutes. The slowest time has been about three hours. For the three hour case, the packaged CT IC 24 was removed several times for cleaning before the copper was exposed. Although the process took about three hours for the longest case, the result was still the desired result of etching through the mold compound to expose the copper with minimal copper removal. The actual process thus may require repeating some of the steps to achieve the desired result.

In the foregoing specification, the invention has been described with reference to specific embodiments. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as a critical, required, or essential feature or element of any or all the claims. As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A method of decapsulating a packaged copper-technology integrated circuit, comprising:

mounting the packaged copper-technology integrated circuit in an etcher for removing a portion of an encapsulant surrounding the packaged copper-technology integrated circuit;

heating a portion of the etcher to a first temperature that is approximately sixty degrees Centigrade or less to raise a temperature of the packaged copper-technology integrated circuit;

mixing fuming nitric acid with fuming sulfuric acid in a ratio from at least three to one to no more than six to one parts fuming nitric acid to fuming sulfuric acid to form an etching mixture;

heating the etching mixture to a second temperature that is approximately sixty degrees Centigrade or less to form a heated etching mixture;

applying the heated etching mixture to the packaged copper-technology integrated circuit to expose copper circuit portions of the packaged copper-technology integrated circuit; and removing the packaged copper-technology integrated circuit from the etcher and cleaning the packaged copper-technology integrated circuit.

2. The method of claim 1 wherein the applying of the heated etching mixture to the packaged copper-technology integrated circuit further comprises:

removing no more than five percent of exposed copper in the packaged copper-technology integrated circuit.

3. The method of claim 1 wherein the etching mixture has a ratio of approximately four to one fuming nitric acid to fuming sulfuric acid.

4. The method of claim 1 wherein the etching mixture is heated to a temperature that is approximately fifty degrees Centigrade.

5. The method of claim 1 further comprising applying the heated etching mixture to the packaged copper-technology integrated circuit for a programmed amount of time that is dependent on material type of the encapsulant.

6. The method of claim 1 wherein the first temperature and the second temperature are substantially equal.

7. The method of claim 1 further comprising:

performing at least one of physical testing or electrical testing of the copper circuit portions of the packaged copper-technology integrated circuit that were exposed.

8. The method of claim 1 further comprising:

removing the portion of the encapsulant that is overlying a circuit die, wires and wirebonds while leaving sufficient copper to permit predetermined physical or electrical testing functionality.

9. A method of exposing copper-technology contained within a packaged integrated circuit, comprising:

mounting the packaged integrated circuit in an etcher for removing a portion of an encapsulant surrounding the packaged integrated circuit;

heating a portion of the etcher to a first temperature that is approximately fifty-five Centigrade or less to raise a temperature of the packaged copper-technology integrated circuit;

mixing fuming nitric acid and fuming sulfuric acid in a mixing chamber coupled to the etcher in a ratio of approximately four parts to one fuming nitric acid to fuming sulfuric acid to form an etching mixture, heating the etching mixture prior to introduction into the etcher to a second temperature that is approximately fatty-five degrees Centigrade or less to form a heated etching mixture;

applying the heated etching mixture to the encapsulant of the integrated circuit to expose at least a portion of the copper-technology in the packaged integrated circuit; and removing the packaged integrated circuit from the etcher and cleaning the packaged integrated circuit.

10. The method of claim 9 further comprising:

directing the heated etching mixture to a portion of the encapsulant primarily overlying an encapsulated integrated circuit die to thereby expose the portion of the copper-technology without removing all encapsulant of the packaged integrated circuit.

11. The method of claim 9 further comprising:

delaying mixing fuming nitric acid and fuming sulfuric acid in the mixing chamber until the portion of the etcher has been heated to the first temperature.

12. The method of claim 9 wherein the portion of the copper-technology in the packaged integrated circuit that is exposed by the heated etching mixture comprises copper bond pads, copper shires, copper conductors and active copper circuitry.

13. A method of exposing copper-technology contained within a packaged integrated circuit comprising:

mounting the packaged integrated circuit in an etcher for removing a portion of an encapsulant surrounding the packaged integrated circuit;

heating a portion of the etcher to a first temperature that is approximately fifty degrees Centigrade, plus or minus five degrees Centigrade, to raise a temperature of the packaged copper-technology integrated circuit;

coupling a source of fuming nitric acid to the etcher;

coupling a source of fuming sulfuric acid to the etcher;

mixing the fuming nitric acid and the fuming sulfuric acid in the etcher in a ratio of approximately four parts to one fuming nitric acid to fuming sulfuric acid to form an etchant;

heating the etchant prior to introduction into an etching chamber to a second temperature that is approximately fifty degrees Centigrade, plus or minus five degrees Centigrade to form a heated etching mixture;

applying the heated etching mixture to the encapsulant of the integrated circuit to expose at least a portion of the copper-technology in the packaged integrated circuit; and removing the packaged integrated circuit from the etcher and cleaning the packaged integrated circuit.

14. The method of claim 13 wherein the first temperature and the second temperature are substantially identical temperatures.

15. The method of claim 13 further comprising:

performing physical tests on the integrated circuit, the physical tests comprising either a wire-pull test or a conductive ball shear test.

16. The method of claim 13 wherein the encapsulant is a molding compound.

* * * * *

UNITED STATES PATENT AND TRADEMARK OFFICE
CERTIFICATE OF CORRECTION

PATENT NO. : 6,709,888 B2
DATED : March 23, 2004
INVENTOR(S) : Julie M. Nadeau

It is certified that error appears in the above-identified patent and that said Letters Patent is hereby corrected as shown below:

Column 5,
Line 22, change "fatty-five degrees" to -- fifty-five degrees --.

Column 6,
Line 2, change "copper shires" to -- copper wires --.

Signed and Sealed this

Twenty-first Day of December, 2004

JON W. DUDAS
*Director of the United States Patent and Trademark Office*